(12) United States Patent
Chamba et al.

(10) Patent No.: US 7,365,030 B2
(45) Date of Patent: Apr. 29, 2008

(54) PROCESS FOR MAKING A WET WIPE USING A CONCENTRATED EMULSION

(75) Inventors: Sylvie Chamba, Bad Soden (DE); George Endel Deckner, Cincinnati, OH (US); Mathias Kurt Herrlein, Hofheim (DE); Antonio Martinez-Campoy, Rüsselshiem (DE)

(73) Assignee: The Procter & Gamble Company, Cincinnati, OH (US)

( * ) Notice: Subject to any disclaimer, the term of this patent is extended or adjusted under 35 U.S.C. 154(b) by 177 days.

(21) Appl. No.: 10/883,339

(22) Filed: Jul. 1, 2004

(65) Prior Publication Data

US 2005/0009431 A1 Jan. 13, 2005

Related U.S. Application Data

(60) Provisional application No. 60/520,032, filed on Nov. 14, 2003, provisional application No. 60/485,847, filed on Jul. 9, 2003.

(51) Int. Cl.
*B32B 27/04* (2006.01)
*B32B 27/02* (2006.01)
*A61F 8/00* (2006.01)

(52) U.S. Cl. ............ 442/123; 442/164; 442/170; 424/70.1

(58) Field of Classification Search ............ 442/123, 442/164, 170
See application file for complete search history.

(56) References Cited

U.S. PATENT DOCUMENTS

| | | | |
|---|---|---|---|
| 4,379,755 A | 4/1983 | Yamada et al. | |
| 4,380,503 A | 4/1983 | Koerner et al. | |
| 4,606,913 A | 8/1986 | Aronson et al. | |
| 4,741,944 A | 5/1988 | Jackson et al. | |
| 4,776,976 A | 10/1988 | Nakamura et al. | |
| 4,865,221 A | 9/1989 | Jackson et al. | |
| 4,904,524 A | 2/1990 | Yoh | |
| 5,085,854 A | 2/1992 | Fakuda et al. | |
| 5,362,418 A | 11/1994 | Yamasaki et al. | |
| 5,538,732 A | 7/1996 | Smith et al. | |
| 5,539,021 A | 7/1996 | Pate et al. | |
| 5,688,842 A | 11/1997 | Pate, III et al. | |
| 5,928,631 A | 7/1999 | Lucas et al. | |
| 5,976,604 A | 11/1999 | Kunieda et al. | |
| 6,410,039 B1 * | 6/2002 | Walker | 424/404 |
| 6,503,526 B1 * | 1/2003 | Krzysik et al. | 424/402 |
| 6,660,778 B1 * | 12/2003 | Durand et al. | 516/53 |
| 2001/0055609 A1 | 12/2001 | Schantz et al. | |
| 2002/0123448 A1 | 9/2002 | Dunn | |
| 2002/0128615 A1 | 9/2002 | Tyrell et al. | |
| 2003/0027738 A1 | 2/2003 | Delambre et al. | |
| 2003/0049290 A1 | 3/2003 | Jha et al. | |
| 2004/0121680 A1 | 6/2004 | Yahiaoui et al. | |

FOREIGN PATENT DOCUMENTS

| | | |
|---|---|---|
| EP | 0328355 A | 8/1989 |
| EP | 0615741 A | 9/1994 |
| EP | 0759291 A | 2/1997 |
| EP | 0 808 151 B1 | 8/2001 |
| WO | WO 97/32559 A1 | 9/1997 |
| WO | WO 99/55303 A | 11/1999 |
| WO | WO 02/41869 A2 | 5/2002 |

OTHER PUBLICATIONS

Lin T.J. et al. "Low-Energy Emulsification. Part VI: Applications in High-Internal Phase Emulsions", Jorunal of the Society Cosmetic Chemists, New York, NY, US, vol. 34, No. 7, Nov. 1984, pp. 357-368, X008022694 Introduction part on p. 357-358 figure 1; table 1.

* cited by examiner

*Primary Examiner*—Lynda Salvatore
(74) *Attorney, Agent, or Firm*—Matthew P. Fitzpatrick; Sarah Ann Dressel; Laura L. Whitmer

(57) ABSTRACT

The present invention provides a process for making a concentrate composition leading to a high internal phase diluted emulsion composition, that can be used for preparation of wet-wipes.

17 Claims, No Drawings

PROCESS FOR MAKING A WET WIPE USING A CONCENTRATED EMULSION

CROSS REFERENCE

This application claims the benefit of U.S. Ser. No. 60/520,032, filed Nov. 14, 2003, and U.S. Ser. No. 60/485,847, filed Jul. 9, 2003.

FIELD OF INVENTION

This invention relates to process for manufacturing wet wipes, in particular to a process for providing a wipe substrate with a lotion. The wet wipes of the invention comprises an emollient, a surfactant as well as, optionally, other substances. The wet wipe of the invention is preferably a piece of substrate with a liquid or semi liquid lotion intended for wiping efficiently and smoothly human body parts.

The process of the invention can be seen as a 3-step process, where a concentrated emulsion composition is first prepared. The concentrated composition can later be diluted and complemented with other compounds. The diluted composition can then be applied to wipes substrate material.

BACKGROUND OF THE INVENTION

Cleansing the skin is a personal hygiene problem not always easily solved. Dry tissue products are the most commonly cleansing product used post-defecation or post-urine release. Dry tissue products are usually referred to as "toilet tissue" or "toilet paper". Beside the use of dry tissue, it is becoming increasingly frequent to use wet wipes for the purpose of cleaning the anus, the perinea, and the peri-anal body area after defecation So called "Wet wipes" are a fibrous structure, generally of thick caliper, impregnated with a composition, usually water or oil-based.

Among those negatives associated with the failure of adequate cleansing are irritation, redness, desquamation, infections, unpleasant odor or other kind of personal discomfort or health related issues. People suffering from pathological conditions (such as hemorrhoids, fissures, cryptitis, etc.) are even more susceptible to those issues and discomfort. For them, as for any persons, cleansing must be efficient in terms of removal of fecal residues and gentle in terms of absence of irritation caused by the cleansing. Wet-Wipes bring a response to that basic need. For example, the Pampers Baby Fresh and regular baby wipes are marketed with a patent marking of U.S. Pat. No. 4,904,524.

The use of emulsions in lotion for wipes is widely spread. Most commonly use emulsion use an oil-in-water type of emulsion, having as key components an oily phase (in the form of an emollient), an emulsifier or surfactant component and an aqueous phase that comprises further additives such as antimicrobial agents.

Many patent documents intend to describe wipes with emulsion based lotions:

In EP808151B1, Blieszner et al, describe a composition for wipes and wipes using a composition that is useful for personal cleansing and for reducing the risk of perineal dermatitis. In WO-0241869, Hsu, Jay, C. et al. describe a paper product treated with oil-in-water emulsions. The paper product contains a lotion, an emollient, a fatty alcohol component in, an emulsifier component, and a skin conditioning component. All components presenting a defined percentage of the lotion and paper product.

U.S. Pat. Nos. 4,741,944 and 4,865,221 provide wet wipes having a liquid in the sheet and/or web. The liquid includes water, benzalkonium chloride, citric acid, disodium phosphate, trisodium ethylene diamine tetraacetic acid, polyethylene glycol-75 lanolin, cocoamphocarboxyglycinate, propylene glycol, methylparaben, propylparaben, butylparaben, polysorbate 20 and fragrance.

General background on emulsions and in particular in High Internal Phase Emulsions and their potential use in cosmetics can be found in:

U.S. Pat. No. 4,606,913 describing high internal phase emulsions having enhanced stability and their use in cosmetics.

U.S. Pat. No. 5,539,021 and U.S. Pat. No. 5,688,842 describing a method for making a high internal phase emulsion without phase inversion.

U.S. Pat. No. 5,362,418 describing an oil-in-water gel-like emulsion a comprising mono-alkyl phosphate salt.

U.S. Pat. No. 5,085,854 describing a translucent cosmetic emulsion comprising mono-alkyl phosphate salt.

In U.S. Pat. No. 4,776,976, Nakamura and Suzuki describe an oil in water emulsion comprising a basic amino acid salt of aliphatic phosphate group.

U.S. Pat. No. 5,976,604 and U.S. Pat. No. 4,379,755 describing an oil-in-water emulsion with high oil content, comprising a sucrose fatty ester.

WO 97/32559 describing a stable dispersion having a bi-liquid foam comprising oil droplets and suitable for cosmetic applications.

Many of the above documents are directed at finding alternatives or improved ways to deliver better wipes performance.

In general, lotion compositions for wet wipes, and more specifically emulsions are manufactured by mixing an emollient compound into an excess of water and a surfactant or emulsifier. This process for making an emulsion however requires stringent process conditions, i.e., a high energy input to homogenize the oil and water phase and e.g., to generate a defined particle size distribution into the aqueous phase: generally a high shear mixing is needed together with the heating of the composition being prepared.

This high-energy input is costly for the manufacturer and requires specific equipment (i.e., significant investment level). Also, the high shear and stringent process conditions represent a significant stress on the ingredients of emulsions conventionally prepared (for example break-down of large molecular weight structures). Moreover the emulsions prepared by such conventional processes are by nature very diluted. Handling, storage and transportation represent significant inconvenience and cost.

Also, it there is a limit in particle size which can be achieved with traditional emulsion making processes (the particle size is the size of the oil droplets in the aqueous solution of the oil-in-water emulsion). Emulsions of low oil droplet size require generally most stringent preparation whereas it has been proven that low oil droplet size induces more desirable end properties for the emulsions.

It has been found that emulsions with small oil droplet size (=small particle size) deliver to the user an increased amount to of the emollient upon application.

There is a need for a wipe providing a smooth, long lasting comfortable feeling to the user. There is also a need for an emulsion composition applied to a wipe that is relatively easy and cost efficient to prepare and preserve. There is additionally a need for a way to prepare such emulsions that would be cost efficient and would enable storage and transportation of the emulsion in a concentrated form.

There is a further need for a process to prepare such wipes comprising an emulsion that would preferably only require low energy input, and in particular low shear and little or no heat input. There is also a need for a process to prepare such wipes comprising an emulsion process that would provide a low shear stress to the ingredients. There is additionally a need for a way to prepare an emulsion exhibiting oil droplets that are of very small dimension and are stable and/or meta-stable.

There is a need for the preparation of an universal emulsion premix or concentrate to which the various additives corresponding to the desired properties could be added subsequently. There is finally a need for a way to prepare such an emulsion combining all or most of the above benefits to a so far unachieved level.

SUMMARY OF THE INVENTION

The present invention describes a process for making a wet wipe comprising lotion composition. More particularly it describes a process for preparing the lotion composition as a concentrated emulsion that can be easily handled, stored and transported. The concentrated emulsion composition can then be diluted with water and complemented with other compounds to obtain the desired final composition that is applied to a wipe substrate. In that respect, the present invention allows to best leverage manufacturing capability by providing a concentrated emulsion that can be diluted into ready-to-use lotion composition.

The composition concentrate obtained by the process of the present invention is a high internal phase concentrate. It leads preferably to a oil-in-water emulsion that exhibits very small oil droplet size, when diluted.

The process is characterized by the fact that it requires only a low level of energy input (for example, low shear and little or no heat input) to insure the formation of a stable and/or meta-stable emulsion composition concentrate, compared to conventional processes.

The process of the present invention creates an oil-in water emulsion composition for wipes that comprises oil droplets of very small size.

In another embodiment, the process of the present invention is characterized by the fact that the rate of addition of the emollient into the surfactant solution (or surfactant solution) is adjusted as such as to not decrease the viscosity of the composition being formed.

All documents cited are, in relevant part, incorporated herein by reference; the citation of any document is not to be construed as an admission that it is prior art with respect to the present invention.

DETAILED DESCRIPTION OF THE INVENTION

Wet-Wipes

The present invention proposes a process for making wet-wipes comprising a lotion composition. Wet wipes or wipes or wet-tissues or body wipes is the general term to describe a piece for material, generally nonwoven material, used to cleanse body parts. In particular most of currently available wipes are intended for the cleaning of the peri-anal area after defecation. Other wipes are available for the cleansing of the face or other body parts. The present invention focuses on wipes for peri-anal (or perineal) area but it not limited to that type of wet wipes. Wet-wipes are generally of sufficient dimension to allow for a convenient handling while being small enough to be easily disposed to the sewage system. The material of the wipes (so called "substrate") is generally soft and flexible, potentially having a structured surface enhancing its cleaning performance. The material is preferably a non-woven material, generally made of synthetic compounds. However, woven materials as well as the use of natural compounds in either woven or nonwoven materials are within the scope of the present invention. In one embodiment of the present invention the substrate comprises a non-woven material comprising fibers selected from the group consisting of polyolefin, polyester, cellulose, rayon, polyamides, polyesteramide, polyvinyl alcohols, and combinations thereof. While in some wet-wipes the texture and material of the wipe are of high relevance to the performance of the wipe, the present invention however focuses on the formation of the composition impregnating the substrate to form the wet-wipes.

Wipes are generally impregnated with a liquid or semi liquid composition, intended to both enhance the cleaning and to provide for a smooth feeling. Other ingredients or actives (for example cosmetic or pharmaceutical active) can be part of the composition.

Generally the composition is of sufficiently low viscosity to impregnate the entire structure of the wipe. In some other instances, the composition can be primarily present at the wipe surface and to a lesser extend in the inner structure of the wipe. In one optional embodiment the composition is releasably carried by the material, that is, the composition is contained either in or on a substrate and is readily releasable from the substrate by applying some force to the substrate, for example, wringing the substrate, or wiping a surface, such as a child's bottom, with the wet-wipe.

Composition

The compositions used in the process of the present invention include the concentrated oil-in-water emulsion composition and the diluted composition. Diluting the former with water forms the latter. With, the exception of the water concentration the components of the diluted composition are the same as the corresponding concentrated oil-in-water emulsion composition. The diluted composition then impregnates the substrate to form the wet-wipe. The concentrated oil-in-water emulsion composition is interchangeably called lotion, soothing lotion, concentrated composition, soothing composition, cleansing or cleansing lotion or composition, emulsion, or emulsion composition. All those terms are hereby used interchangeably and indicate the, at least-dual basic function of the composition of the present invention: enhancing cleansing and delivering skin soothing effect.

In most of its embodiments, the composition of the present invention comprises, but is not limited to:
  An emollient
  A surfactant and/or an emulsifier; and
  Water.
  Other ingredients may be incorporated into the composition these include, but are not limited to, are rheology modifiers, soothing agents and preservatives.

Emollient

Common dictionaries define "emollient" as "something that softens or soothes. Their function in a wet-wipe include (1) to improve the glide of the wipe on the skin, by enhancing the lubrication and thus decreasing the abrasion of the skin, (2) to hydrate the residues (for example fecal residues or dried urine residues), thus enhancing their removal from the skin, (3) to hydrate the skin, thus reducing its dryness and irritation while improving its flexibility under the wiping movement, (4) to protect the skin from later irritation (for example, caused by the friction of the underwear) as the emollient is deposited onto the skin and remain at its surface as a thin protective layer.

Preferable emollients used by the process of the present invention are silicon based. Silicones based emollients are organo-silicone based polymers with repeating silioxane (Si—O) units. Silicones based emollients of the present invention are hydrophobic and exist in a wide range of possible molecular weights. They include linear, cyclic and cross-linked varieties. Silicone oils are generally chemically inert and usually have usually a high flash point. Due to their low surface tension, silicone oils are easily spread able and have high surface activity. Examples of silicon oil of the present invention include, but are not limited to: Cyclomethicones, Dimethicones, Phenyl-modified silicones, Alkyl-modified silicones, Silicones resins, Silica and combinations thereof.

Other emollients useful in the present invention include unsaturated esters or fatty esters, such as Caprylic capric triglycerides in combination with bis-PEG/PPG-16/16PEG/PPG-16/16 Dimethicone $C_{12}$-$C_{15}$ Alkylbenzoate.

The amount of emollient that can be included in the lotion composition concentrate and in the diluted composition will depend on a variety of factors, including the particular emollient involved, and the lotion-like benefits desired, the other components in the lotion composition. In one embodiment, the concentrated composition comprises from about 75% to about 99% of the emollient, more preferably from about 80% to about 94%, and even more preferably from about 85% to about 92% of the emollient (all % herein are weight to weight % unless otherwise specified).

Also preferably the emollient of the present invention has a solubility parameter between about 5 and about 12, more preferably between about 5 and about 9.

Emulsifier/Surfactant

The concentrated composition and the diluted composition also include an emulsifier such as those are known in the art for forming oil-in-water emulsions.

The emulsifier can be a mixture of chemical compounds and include a surfactant. The preferred emulsifiers are those acting as well as a surfactant. Both terms, surfactant and emulsifier are used interchangeably in this document. Mixtures of emulsifiers may be used. In the present invention, the surfactant is used as a solution of least about 25% surfactant content (w/w). In one embodiment the surfactant is used as a pure form (100% w/w). The surfactant solutions of the present invention can be aqueous solution or non-aqueous solutions. The terms surfactant, emulsifier, surfactant solution are used herein interchangeably. The emulsifier can be a polymeric emulsifier.

In one embodiment of the present invention the emulsifier has a viscosity of less than about 15,000 cps at about 25 degrees Celsius of a 1% aqueous solution of the emulsifier as measured by a Brookfield apparatus as described in the method part of this document. More preferably the viscosity is less than about 10,000 cps under the same conditions.

The emulsifier is employed in an amount effective to emulsify the emollient and non-water-soluble oils that are be present in the composition. In one embodiment of the present invention, the amount of emulsifier in the concentrated composition ranges from about 1% to about 25%, preferably from about 6% to about 20%, more preferably about 8% to about 15% (based on the weight of emollient over the weight of the concentrated composition).

In one embodiment of the present invention, the concentrated composition has ratio between the amount of surfactant and emollient between about 1:9 and about 1:72 (on a weight/weight basis), more preferably between about 1:14 to about 1:30 (w/w).

Surfactant/emulsifiers having a low surface tension are preferred for the present invention. Other characteristics of preferable surfactant/emulsifier include high polarity and a non-ionic nature.

Other Optional Components of the Composition

The composition of the claimed invention can optionally include an adjunct ingredient. The adjunct ingredient may include a wide range of additional ingredients such as, but not limited to perfumes, soothing agents, fragrances, preservative, rheology modifiers, moisturizers, texturers, colorants, medically active ingredients, in particular healing actives and skin protectants. Combinations of adjunct ingredients are also within the scope of the present invention.

Soothing Agent

Soothing agent can be added to the composition of the present invention. Soothing agents are compound having the ability to reduce the irritation or stinging effect of some chemicals. Soothing agents can be of a variety of chemical classes. Soothing agents can have a variety of mode of actions to neutralize the effects of the skin irritants especially for paraben based preservative systems. For example antioxidants can be soothing agents for oxidants. Buffers can be soothing agents neutralizing the stinging effect on skin of acids or bases. It is to be noted that emollients can also be soothing agents. Soothing agent acting against the stinging/irritation effect of some preservatives are preferred. Those soothing agents can be emollients or surfactants helping, for example, the solubilization or the micellization of the preservatives.

The preferred soothing agents of the present invention are (a) ethoxylated surface active compounds, more preferably those having a ethoxylation number below about 60, and (b) polymers, more preferably Polyvinylpirrolidone (PVP) and/or N-Vinylcaprolactam Homopolymer (PVC), and (c) Phospholipids, more preferably phospholipids complexed with other functional ingredients as e.g., fatty acids and organo-silicones.

Preservative

Optionally, the composition used by the process of the present invention can include a preservative or a mixture of preservatives. The need to control microbiological growth in personal care products is known to be particularly acute in water based products such as non-ionic oil-in-water emulsions and in pre-impregnated wipes such as baby wipes.

The process of the present invention can comprises providing a preservative compound or more preferably a combination of preservative compounds acting together as a preservative system. Preservative and preservative systems are used interchangeably in the present document to indicate one unique or a multiplicity of preservative compounds.

As preservative it is understood a chemical or natural compound or a multiplicity of compounds reducing the growth of microorganisms, thus enabling a longer shelf life for the pack of wipes (opened or not opened) as well as creating a environment with reduced growth of microorganisms when transferred to the skin during the wiping process.

The preservative of the present invention (or preservative system) can comprise one or more of the parabens class of preservatives. Preferably the preservative is selected from the list of Methylparaben, Ethylparaben, Propylparaben, Butylparaben, Isobutylparaben or a combination thereof.

The total concentration of paraben preservatives encompassed by the present invention is preferably lower than about 1%, more preferably lower than about 0.5%, even more preferably lower than about 0.3% (it is to be noted that legal requirements may restrict those ranges in practice). The minimum amount of paraben antimicrobial is any amount sufficient to obtain the desired preservation of the composition, in most embodiments of the invention more than 0.001% (w/w).

Rheology Modifier

Rheology modifiers are compounds that increase the viscosity of the composition at lower temperatures as well as at process temperatures. Rheology modifiers or suspending agents or stabilizers also provide "structure" to the compositions to prevent settling out (separation) of insoluble and partially soluble components. Other components or additives of the compositions may affect the temperature viscosity/rheology of the compositions.

The effect and advantage of rheology modifiers are in particular described in US20020128621A1 entitled "Absorbent articles with simplified compositions having good stability" published on Sep. 12, 2002, filed on Dec. 21, 2001, by Kruchoski et al., and US20020128615A1 entitled "Absorbent articles with non-aqueous compositions containing anionic polymers" published on Sep. 12, 2002, filed on Dec. 22, 2001, by Tyrrell et al.

In addition to stabilizing the suspension of insoluble and partially soluble components, the rheology modifiers also help to stabilize the composition on the wipe and enhance the transfer of lotion to the skin: The wiping movement increases the shear and pressure therefore decreasing the viscosity of the lotion and enabling a better transfer to the skin as well as a better lubrication effect.

Additionally, the rheology modifier helps to preserve a homogeneous distribution of the composition within the wipe stack: Any fluid composition has a tendency to migrate to the lower part of the wipes stack during prolonged storage. This effect creates an upper zone of the stack having less composition than the bottom part. This is seen as a sign of relatively low quality by the users.

Preferred rheology modifiers exhibit low initial viscosity and high yield. Particularly suited for the present invention are rheology modifiers such as, but not limited to:

Blends of material as are available from Uniqema GmbH&Co. KG, of Emmerich, Germany under the trade name ARLATONE. Particularly preferred are ARLATONE V-175 which is a blend of sucrose palmitate, glyceryl stearate, glyceryl stearate citrate, sucrose, mannan, and xanthan gum, and ARLATONE V-100 which is a blend of Steareth-100, Steareth-2, glyceryl stearate citrate, sucrose, mannan, and xanthan gum.

Blends of material as are available from Seppic France of Paris, France as SIMULGEL. Particularly preferred is SIMULGEL NS which comprises blends of hydroxyethylacrylate/sodium acryloyldimethyl taurate copolymer and squalene and polysorbate 60, Sodium acrylate/Sodium acryloyldimethyltaurate copolymer and polyisobutene and caprylyl capryl glucoside, Acrylate copolymers, such as but not limited to Acrylates/Acrylamide Copolymer, mineral oil, and Polysorbate 85.

Acrylate homopolymers, Acrylate crosspolymers, such as but not limited to Acrylate/$C_{10-30}$ Alkyl Acrylate crosspolymers, carbomers, such as but not limited to acrylic acid cross linked with one or more allyl ether, such as but not limited to allyl ethers of pentaerythritol, allyl ethers of sucrose, allyl ethers of propylene, and combinations thereof as are available as the Carbopol® 900 series from Noveon, Inc. of Cleveland, Ohio (e.g., Carbopol® 954).

Naturally occurring polymers such as xantham gum, Galactoarabinan and other polysaccharides.

Combinations of the above rheology modifiers.

Examples, of commercially available rheology modifiers include but are not limited to, Ultrez-10, a carbomer, and Pemulen TR-2, an Acrylate crosspolymers, both of which are available from Noveon, Cleveland Ohio, USA, and Keltrol, a xanthan gum, available from available from CP Kelco San Diego Calif., USA.

When present rheology modifiers are typically present in the dilute composition at a weight/weight % (w/w) of preferably from about 0.01% to about 3%, more preferably from about 0.015% to about 2%, even more preferably from about 0.02% to about 1%.

Concentrated Composition

The concentrated composition of the present invention (also called herein interchangeably concentrate, concentrate composition, concentrated emulsion, emulsion concentrate) has a water content of less than about 30% (w/w), preferably the water content is less than about 20% (w/w), more preferably less than about 10% (w/w). The minimum amount of water is, in most embodiments of the present invention, more than about 0.1%.

In one embodiment of the present invention the average particle size (=emollient droplet size) is less than about 12 microns, more preferably less than about 10, even more preferably less than about 5 microns, even more preferably still less than about 1 micron. To this corresponds an average particle size of the diluted composition having the same values, also some variation in the particle size can be observe during/after the dilution step.

Examples of compositions that can be manufactured by the process of the present invention are described in co-pending U.S. Provisional Patent Application No. 60/520,031 entitled "A COMPOSITION FOR WET WIPES THAT ENHANCES THE EFFICACY OF CLEANSING WHILE BEING GENTLE TO THE SKIN" by George Deckner et al., Procter & Gamble Attorney Docket No. CM2755P2Q and filed on Nov. 14, 2003.

Article of Commerce

In one embodiment of the present invention an article of commerce is provided. The article of commerce of the present invention typically comprises (a) a container as described herein, and (b) at least wet wipe as described herein.

Containers useful in the present article include but are not limited, for example, PET tubs, flow wrap pouches, precut sachets for individually packed cleansing mitt, and other packaging known in the art as suitable for a nonwoven article. Additionally, the container can also be manufactured to facilitate removal of individual cleansing wet wipes.

The container can be made of any suitable material or materials, and can be manufactured in any suitable manner. For example, the container can be made of polystyrene, polypropylene, PET, POET, polyethylene, polyester, polyvinyl alcohol, or the like. The containers may also be made of mixtures of materials. The containers can be manufactured by, for example, a vacuum molding process or an injection molding process, or any suitable process.

Additional information on containers, as well as additional option components for containers, including but not limited to: container bodies; lids; containers features, such as but not limited to, attachments of lids, hinges, zippers, securing means; and the like, can be found in U.S. Pat. Nos. Des 451,279; Des 437,686; Des 443,508; Des 443,451; Des 421,901; Des 421,902; Des 416,794; Des 414,637; Des 445,329; 3,982,659; 3,967,756; 3,986,479; 3,994,417; 6,269,970; 5,785,179; 5,366,104; 5,322,178; 5,050,737; 4,971,220; 6,296,144; 6,315,114; 4,840,270; 4,471,881; 5,647,506; 6,401,968; 6,269,969; 6,412,634; 5,791,465; 6,092,690; and 6,092,690; U.S. Patent Application Publication No. 2002/0064323 published on May 30, 2002, inventor Chin; and WO 00/27268 published on May 18, 2000, and assigned to The Procter & Gamble Co.; WO 02/14172 published on Feb. 21, 2002, and assigned to The Procter & Gamble Co.; and WO 99/55213 published on Nov. 4, 1999, and assigned to The Procter & Gamble Co.

Shear Rate

On contrary to the conventional emulsification process using very high shear rate, the present invention allows for (and is best practices when) using a preferred shear rate below about 10,000 s$^{-1}$, more preferably below 1,000 s$^{-1}$, and even more preferably below 100 s$^{-1}$ (shear rate is measured according to the method described herein).

Rate of Addition of the Emollient

In one embodiment of the present invention, the rate of addition of the emollient into the surfactant solution is chosen as such as to not decrease the viscosity of the concentrated composition being formed.

Converting

The process of the present invention comprises a step of providing a wipe substrate and providing a quantity of the diluted composition onto the substrate. This step is referred as a converting step. Any known type of substrate can be used in the converting step, preferably substrate are of synthetic nonwoven nature but can also include (or be primarily constituted from) cellulosic fibers. The step of providing the diluted composition onto the wipes substrate can be achieved by any conventional application process, such as (but not limited to) spraying, printing, and coating (for example with the use of a curtain coater or a slot coater).

EXAMPLES

Examples A and B are examples of the first process step of the present invention, where a concentrated emulsion mix is prepared.

Example A (The Equipment Used is Described Therein for a Batch Size of 100 kg.)

A mix-tank is equipped with a top-entry double-stage agitator, designed such as the ratio Z/T with Z being the maximum height of liquid in the mix-tank and T being the mix-tank diameter, is comprised between 0.80 and 1.2 (for instance, T=546 mm), and such as the ratio D/T with D being the impeller diameter and T as described above, is 0.66. The top entry double stage agitator will be a Wide Blade Hydrofoil having 4 blades per stage each having a high angle of attack (for instance a Philadelphia 4HS45) and will be positioned such as the ratio $C_1$/T with $C_1$ being the distance between the bottom of the vessel and the middle of the lowest agitator stage (for instance $C_1$=70 mm) and T as described above is between 0.12 and 0.15, such as the ratio $C_2$/T with $C_2$ being the distance between the bottom of the vessel and the middle of the highest agitator stage and T as described above is between 0.5 and 0.6.

The formulation of the composition is described in Table A

TABLE A

| Component | Amount (% by weight) |
|---|---|
| (1) Plantacare2000UP ™* | 10.5 |
| (2) DC 1501 ™** | 89.5 |

*Plantacare2000UP ™ comprises about 50% surfactant (Decylglucoside) in water, and is commercialized by Cognis GmbH, 40551 Düsseldorf, Germany, www.cognis.com.
DC 1501 ™ comprises Cyclopentasiloxane Dimethiconol and is commercialized by Dow Corning, 65201 Wiesbaden, Germany www.dowcorning.com.

Process Description (a) Add the whole amount of (1) in the vessel. The lower blade of the agitator reaches the surface of the agitator (liquid level is $\geq C_1$). Agitation process is started at N=200 rpm.

(b) Start continuous addition of (2) into (1) at flow-rate comprised between 260 and 340 kg/h. The flow-rate must be slow enough to allow good incorporation of (2) into (1). The agitator speed is gradually increased up to 300 rpm. When 70-80% of (2) in weight is added, the addition flow-rate will decrease to a range comprised between 180 and 230 kg/h to ensure good incorporation of the remaining of (2) in the composition. The agitator speed can be increased to 350 rpm at the end of addition for better incorporation.

(c) At the end of addition, the composition is stirred for an extra 2 min. The batch can be discharged for further processing.

The calculated shear-rate is 88 s$^{-1}$ at 350 rpm.

Example B (The Equipment Used is Described Therein for a Batch Size of 20 kg)

A mix-tank is equipped with a top-entry double-stage agitator, designed such as the ratio Z/T with Z being the maximum height of liquid in the mix-tank and T being the mix-tank diameter, is comprised between 0.80 and 1.2 (for example T=300 mm and Z=300 mm), and such as the ratio D/T with D being the impeller diameter and T as described above, is 0.66 (for example D=200 mm). The top entry double stage agitator will be a Pitch Blade Turbine 45° having 4 blades per stage and will be positioned such as the ratio $C_1$/T with $C_1$ being the distance between the bottom of the vessel and the middle of the lowest agitator stage and T as described above is between 0.12 and 0.15, such as the ratio $C_2$/T with $C_2$ being the distance between the bottom of the vessel and the middle of the highest agitator stage and T as described above is between 0.5 and 0.6.

The formulation of the compositon is described in Table B

TABLE B

| Component | Amount (% by weight) |
| --- | --- |
| (1) Plantacare2000UP ™* | 10 |
| (2) Abil Care 85 ™** | 90 |

*Plantacare2000UP ™ comprises about 50% surfactant (Decylglucoside) in water, and is commercialized by Cognis GmbH, 40551 Düsseldorf, Germany, www.cognis.com.
**Abil Care 85 ™ comprises Bis-PEG/PPG-16/16 PEG/PPG Dimethicone Caprylic Capric triglyceride and is commercialized by Goldschmidt/Degussa, Goldschmidt AG, 45127 Essen, Germany www.goldschmidt.com.

Process Description
(a) Add the whole amount of (1) in the vessel. The lower blade of the agitator reaches the surface of the agitator (liquid level is $\geq C_1$). Agitation process is started at 130 rpm.
(b) Start continuous addition of (2) into (1) at a flow-rate comprised between 60 and 65 kg/h. The addition flow-rate must be low enough to allow good incorporation of (2) into (1). The addition flow-rate is increased gradually. After ⅓ of the amount of (2) is added, the flow-rate can be increased to 90 kg/h. After ⅔ of the amount of (2) is added, the flow-rate can be increased to 120 kg/h.
(c) At the end of addition, the composition is stirred for another extra minute at the same speed (130 rpm). The batch can then be discharged for further processing.

The calculated shear rate is 35 $s^{-1}$ at 155 rpm.

Examples C and D

Examples C and D are examples of the second process step of the present invention where the concentrated emulsion mix is diluted in water with additional ingredients. (The equipment used is described therein for a batch size of 750 kg.)

A mix-tank is equipped with a top-entry double-stage agitator, designed such as the ratio Z/T with Z being the maximum height of liquid in the mix-tank and T being the mix-tank diameter, is comprised between 0.80 and 1.2, and such as the ratio D/T with D being the impeller diameter and T as described above, is between 0.3 and 0.4 (for instance 0.33). The top entry double stage agitator will be a Pitch Blade Turbine 45° having 4 blades per stage and will be positioned such as the ratio $C_1/T$ with $C_1$ being the distance between the bottom of the vessel and the middle of the lowest agitator stage and T as described above is between 0.25 and 0.35, such as the ratio $C_2/T$ with $C_2$ being the distance between the bottom of the vessel and the middle of the highest agitator stage and T as described above is between 0.5 and 0.6.

Example C

The formulation of the composition is described in Table C.

TABLE C

| Component | Amount (% by weight) |
| --- | --- |
| (1) Disodium EDTA | 0.10 |
| (2) Arlatone-V 175 ™* | 0.80 |
| (3) DC 1501 ™** | 0.45 |
| (4) Plantacare2000UP ™*** | 0.05 |
| (5) 1.2 Propylengylcol | 1.50 |
| (6) Sodium benzoate | 0.20 |
| (7) Methylparaben | 0.15 |
| (8) Propylparaben | 0.05 |
| (9) Ethylparaben | 0.05 |
| (10) PEG-40 Hydrogenated Castor Oil | 0.80 |
| (11) Perfume | 0.05 |
| (12) Purified water | balance |
| Total | 100.00 |

*DC 1501 ™ comprises Cyclopentasiloxane Dimethiconol and is commercialized by Dow Corning, 65201 Wiesbaden, Germany www.dowcorning.com.
**Arlatone-V 175 ™ comprises sucrose palmitate, glyceryl stearate, glyceryl stearate citrate, sucrose, mannan, xanthan gum and is commercialized by Uniqema GmbH&Co. KG, 46429 Emmerich, Germany, www.uniqema.com.
**Plantacare2000UP ™ comprises about 50% surfactant (Decylglucoside) in water, and is commercialized by Cognis GmbH, 40551 Düsseldorf, Germany, www.cognis.com.

Process Description

A mixing time of about 2 min is allowed in between the process steps.

a—Ingredient (12) is added into the vessel. Agitation is started at 206 rpm and maintained through the whole process.
b—Ingredients (5), (6), (7), (8) and (9) are delivered in a premix form. The amount of ingredient (10) is added into the weighed out quantity of the above-mentioned premix and stirred for 15 min with a propeller stirrer.
c—A Triblender™ F2116 MD MBV B40 equipment is connected on a re-circulation loop and a water flow is pumped through at a flow rate of about 5100 kg/h. Ingredient (2) is added via the funnel of the TriBlender at a speed sufficient for suction. An extra stirring time of 10 min is allowed for homogeneous dispersion.
d—Ingredients (3) and (4) were mixed together as described in Example A. The resulting composition of Example A is added into the vessel while stirring is increased at 220 rpm. An extra 5 min of stirring time is allowed for good dispersion.
e—The premix prepared in step b—is added into the vessel. An extra 3 min of stirring time is allowed.
f—Ingredient (11) is added into the vessel. An extra 2 min of stirring time is allowed for good dispersion.
g—Ingredient (1) is added into the vessel. An extra stirring time of 5 min is allowed before end of batch.
h—The composition can be discharged for further processing.

Example D

The formulation for the composition is described in table D:

TABLE D

| Component | Amount (% by weight) |
| --- | --- |
| (1) Disodium EDTA | 0.10 |
| (2) Arlatone-V 175 ™* | 0.80 |
| (3) Abil Care 85 ™** | 0.45 |

TABLE D-continued

| Component | Amount (% by weight) |
|---|---|
| (4) Plantacare2000UP ™*** | 0.05 |
| (5) 1.2 Propylengylcol | 1.50 |
| (6) Sodium benzoate | 0.20 |
| (7) Methylparaben | 0.15 |
| (8) Propylparaben | 0.05 |
| (9) Ethylparaben | 0.05 |
| (10) PEG-40 Hydrogenated Castor Oil | 0.80 |
| (11) Perfume | 0.05 |
| (12) Purified water | Balance |
| Total | 100.00 |

*Arlatone-V 175 ™ comprises sucrose palmitate, glyceryl stearate, glyceryl stearate citrate, sucrose, mannan, xanthan gum and is commercialized by Uniqema GmbH&Co. KG, 46429 Emmerich, Germany, www.uniqema.com.
**Abil Care 85 ™ comprises Bis-PEG/PPG-16/16 PEG/PPG Dimethicone Caprylic Capric triglyceride and is commercialized by Goldschmidt/Degussa, Goldschmdit AG, 45127 Essen, Germany www.goldschmidt.com.
***Plantacare2000UP ™ comprises about 50% surfactant (Decylglucoside) in water, and is commercialized by Cognis GmbH, 40551 Düsseldorf, Germany, www.cognis.com.

Process Description

A mixing time of about 2 min is allowed in between each process steps.

a—Ingredient (12) is added into the vessel. Agitation is started at 206 rpm and maintained through the whole process.
b—Ingredients (5), (6), (7), (8) and (9) are delivered in a premix form. The amount of ingredient (10) is added into the weighed out quantity of the above-mentioned premix and stirred for 15 min with a propeller stirrer.
c—A Triblender™ F2116 MD MBV B40 equipment is connected on a re-circulation loop and a water flow is pumped through at a flow rate of about 5100 kg/h. Ingredient (2) is added via the funnel of the TriBlender at a speed sufficient for suction. An extra stirring time of 5 min is allowed for homogeneous dispersion.
d—Ingredients (3) and (4) were mixed together as described in Example B. The resulting composition of Example B is added into the vessel. An extra 5 min of stirring time is allowed for good dispersion.
e—The premix prepared in step b— is added into the vessel.
f—Ingredient (11) is added into the vessel. An extra 2 min of stirring time is allowed for good dispersion.
g—Ingredient (1) is added into the vessel. An extra stirring time of 5 min is allowed before end of batch.
h—The composition can be discharged for further processing.

Example E

Example E is an example of the third process step of the present invention, where the diluted composition is applied to a wipe substrate material. The substrate is a nonwoven substrate comprising 60% (w/w) polypropylene fibers and 40% (w/w) viscose fibers and having a average fiber lengths being about 38mm to 40 mm (available for example from PGI, USA).

The wipe substrate material is unwinded at a constant speed from the mother roll to a folding plate. On the unwind path, the substrate material moves against a slot coater with a slot size of 200 microns. The diluted composition as prepared in example C or D is pumped through the slot coder at a flow rate designed such as to ensure a lotion load of 3.0 g of lotion per gram of substrate. The wetted substrate material is folded on the folding board and cut to the size of the wipes.

The water used in the examples of this invention as well as in its description, methods and teaching is water of cosmetic grade or pharmaceutical grade, preferably deionized water, interchangeably referred to as "purified water" or "water".

Methods

Generation of Viscosity Curve to Calculate the K Value and Shear Rate Index (n)

The samples are run on a TA Instruments AR2000 Series Rheometer (New Castle, Del., USA, www.tainst.com), with a cone/plate geometry, tooling: 40 mm, 2° cone. The software used for analysis is TA Rheology Advantage, version 4.1.2. The flow curve method used is a continuous, shear rate controlled ramp from 1 to 1000 $sec^{-1}$ for 5 min at 25° C. The yield stress method used is a continuous shear stress controlled ramp from 200 to 400 Pa for 5 min at 24° C.

The viscosity curve is generated as follows: Approximately 3 ml of sample is placed on a temperature controlled Peltier plate and the cone tooling compresses the sample to its truncating gap. The sample is forced to flow by applying a shear stress controlled by the method. The applied stress is divided by the corresponding shear rate (determined by the rpm and the geometry of the tooling) to generate the viscosity curve. The K and n values were generated via Power-Law model from 2 to 50 $sec^{-1}$.

Shear Rate

The process described therein describes the mixing of the components of the composition at a low shear rate versus commonly used process. The shear rate is calculated as follows:

Given the impeller configuration and dimensions and the mixing vessel dimensions described as Z being the maximum height of liquid in the vessel, T being the diameter of the vessel, D being the diameter of the impeller, $C_1$ being the distance between the bottom of the vessel and the middle of the lowest agitator stage, $C_2$ being the distance between the bottom of the vessel and the middle of the highest agitator stage, Given the composition properties (specific gravity, K and shear index n determined with the viscosity curve), Given the agitation speed N in rpm, The shear rate is calculated based on the Metzner & Otto Concept for non-Newtonian fluids. ("Mixing in the Process Industries" Second Edition by N. Harnby, M. F. Edwards and A. W. Nienow. Chapter 8, pg 140-145, 1992).

Measurement of Oil Droplet Size

The used method to measure the particle size distribution of lotions is the Horiba LA-910. This analyzer measures the particle size distribution by scattering technique. When light goes into a spherical particle of r diameter, three types of light will be emitted.

Light which reflects at the outer surface of the particle. Light which passes through the inside of the particle and then reflects at the inner surface of the particle. Light which passes through the inside of the particle and then reflects when it goes out.

Device Details and Settings

| Device: | Horiba LA-910 | |
|---|---|---|
| Standard measure conditions: | Agitation speed | 2 |
| | Circulation speed | 1 |
| | Ultra Sonic speed | 1 min 0 |
| | Sonic Works during Measuring | NO |
| | Waiting time after Ultra Sonic | 0 sec |
| | Sampling times | 15 |
| | Form of distribution | Standard |
| | Type of Dispersant | Deionized water |
| | Form of Distribution | Standard |
| | Relative Refractive Index | 1.14-0.00i |
| Address: | Horiba Europe GmbH | |
| | 65843 Sulzbach/Ts., Germany | |
| | www.horiba.com | |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a wet-wipe comprising the steps of:
   (A) preparing a concentrated emulsion composition, said step of preparing a concentrated emulsion composition comprising the steps of:
      (a) combining an emollient and surfactant solution to form a combination, wherein said surfactant solution comprises water and at least about 25% w/w of a surfactant;
      (b) mixing said combination at a shear rate of less than about 10000 $s^{-1}$ to obtain a substantially homogenous and concentrated emulsion composition, wherein the water content of said concentrated emulsion composition is less than about 30% w/w;
   (B) preparing a diluted composition by diluting said concentrated emulsion composition with water; and
   (C) providing a wipe substrate and providing a quantity of said diluted composition onto said wipe substrate.

2. The process of claim 1 wherein water is added during said combining step.

3. The process of claim 1 wherein said concentrated emulsion composition has an average emollient droplet size of less than about 12 micrometers, when diluted into an excess of water.

4. The process of claim 1 wherein said combining step is performed at a temperature below about 40° C.

5. The process of claim 1 wherein said mixing step is performed at a shear rate of less than about 100 $s^-$.

6. The process of claim 1 such that the rate of addition of said emollient into said surfactant solution is selected so as to not decrease the viscosity of said concentrated emulsion composition.

7. The process of claim 6 wherein said emollient has a solubility parameter between about 5 and about 12.

8. The process of claim 6 wherein said emollient comprises an oily compound and an emulsifier.

9. The process of claim 1 wherein said concentrated emulsion composition has a surfactant to emollient ratio (w/w) between about 1:9 and about 1:72 w/w.

10. The process of claim 1 wherein said surfactant is substantially soluble in water at 25 degrees Celsius, and a 1% by weight aqueous solution of said surfactant has a viscosity of less than about 15,000 cps at 25° C. and said surfactant is selected from the group consisting of non-ionic, amphoteric, anionic, cationic, and combination thereof.

11. The process of claim 1 further comprising a step (D) of adding an adjunct ingredient into said concentrated emulsion composition or into said diluted composition.

12. The process of claim 11 wherein said adjunct ingredient is selected from the group consisting of rheology modifiers, preservatives, perfume, plant extract, moisturizer, cosmetic active, pharmaceutically active, or a mixture thereof.

13. The process of claim 12 wherein said rheology modifier is selected from the group consisting of a blend of sucrose palmitate, glyceryl stearate, glyceryl stearate citrate, mannan, and xanthan gum; blends comprising sodium acryloyldimethyl taurate copolymers: Acrylate homopolyers; Acrylamide Crosspolymers; Galactoarabinan; xanthan gum and combinations thereof.

14. The process of claim 12 wherein said emollient is selected from the group consisting of Dimethicone, Cyclopentasiloxane Dimethiconol, Caprylic/Capric Triglyceride, $C_{12}$-$C_{15}$ Alykylbenzoate, and combinations thereof.

15. The process of claim 12 wherein said preservatives is selected from the group consisting of Methylparaben, Ethylparaben, Propylparaben, Butylparaben, Isobutylparaben and combinations thereof.

16. The process of claim 1 wherein said wipe substrate comprises fibers selected from the group consisting of polyolefin, polyester, cellulose, rayon, polyamides, polyesteramide, polyvinyl alcohols, and combinations thereof.

17. A wet-wipe prepared according to process of claim 1.

* * * * *

UNITED STATES PATENT AND TRADEMARK OFFICE
CERTIFICATE OF CORRECTION

PATENT NO. : 7,365,030 B2  
APPLICATION NO. : 10/883339  
DATED : April 29, 2008  
INVENTOR(S) : Sylvie Chamba et al.

Page 1 of 1

It is certified that error appears in the above-identified patent and that said Letters Patent is hereby corrected as shown below:

Col. 16, line 4;

Delete "100 s" and insert -- 100 s$^{-1}$ --.

Col. 16, line 36;

Delete "copolymers:" and insert -- copolymers; --.

Col. 16, line 51;

Delete "17. A wet-wipe prepared according to process of claim 1.".

Signed and Sealed this

Thirtieth Day of December, 2008

JON W. DUDAS  
*Director of the United States Patent and Trademark Office*